(12) United States Patent
Swaerd-Nordmo et al.

(10) Patent No.: US 6,562,320 B1
(45) Date of Patent: May 13, 2003

(54) THERMALLY STABILIZED CONTRAST AGENT

(75) Inventors: Marit Swaerd-Nordmo, Oslo (NO); Per Helge Gulliksen, Oslo (NO); Jorunn Undheim Braenden, Oslo (NO); Anne Kjersti Fahlvik, Oslo (NO)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/604,276

(22) Filed: Jun. 26, 2000

Related U.S. Application Data

(62) Division of application No. 09/078,711, filed on May 14, 1998, now Pat. No. 6,165,442, which is a continuation of application No. PCT/GB97/00458, filed on Feb. 19, 1997.
(60) Provisional application No. 60/046,652, filed on May 16, 1997.

(30) Foreign Application Priority Data

| Feb. 19, 1996 | (GB) | 9603466 |
| Jul. 6, 1996 | (GB) | 9611894 |
| Nov. 29, 1996 | (GB) | 9624919 |

(51) Int. Cl.[7] ................................ A61B 8/00
(52) U.S. Cl. ................. 424/9.52; 424/9.5; 424/9.51
(58) Field of Search ................ 424/9.52, 9.51, 424/9.5; 516/11, 77; 600/441, 458

(56) References Cited

U.S. PATENT DOCUMENTS

| 4,642,903 A | | 2/1987 | Davies | |
| 4,857,319 A | | 8/1989 | Crowe | |
| 4,880,635 A | * | 11/1989 | Janoff et al. | 424/450 |
| 5,158,935 A | * | 10/1992 | Nascimento et al. | 514/12 |
| 5,271,928 A | * | 12/1993 | Schneider et al. | 424/9.52 |
| 5,542,935 A | * | 8/1996 | Unger et al. | 604/190 |
| 5,811,118 A | * | 9/1998 | Ostro et al. | 424/450 |
| 5,830,430 A | * | 11/1998 | Unger et al. | 424/1.21 |

FOREIGN PATENT DOCUMENTS

| JP | 06 211 645 A | 8/1994 |

OTHER PUBLICATIONS

Database WPI Section Ch, Week 9435, Derwent Publications Ltd., London, XP002032806 & JP 06 211 645 A, Aug. 2, 1994, (Mitsubishi Kasei Corp).

* cited by examiner

*Primary Examiner*—Michael G. Hartley
(74) *Attorney, Agent, or Firm*—Robert F. Chisholm; Royal N. Ronning, Jr.; Stephen G. Ryan

(57) ABSTRACT

This invention relates to a freeze-dried vesicle containing ultrasound contrast agent containing a freeze-drying stabilizer and thermally stable at temperatures in excess of 20° C.

17 Claims, No Drawings

THERMALLY STABILIZED CONTRAST AGENT

This application is a divisional application of pending U.S. application Ser. No. 09/078,711, filed May 14, 1998, now U.S. Pat. No. 6,165,442, which is a continuation of PCT/GB97/00458, filed Feb. 19,1997, and claims benefit of U.S. provisional application No. 60/046,652, filed May 16, 1997.

This invention relates to thermally stabilized freeze-dried vesicle containing ultrasound contrast agents and a process for their preparation.

Vesicles (the term is used herein to denote unilamellar and multilamellar structures, eg. structures referred to variously as liposomes, micelles, microbubbles and microballoons) are frequently used as a means for delivering therapeutically or diagnostically active agents. In the field of ultrasound imaging contrast media, vesicles containing materials (herein referred to as vesicular materials) which are gaseous at body temperatures may be used as echogenic contrast agents, particularly for administration into the vasculature.

Vesicular contrast media will generally be administered in the form of an aqueous dispersion containing a low concentration of the vesicles relative to the aqueous carrier medium. Accordingly storage and transportation of such vesicular contrast agents is made significantly more efficient if the vesicles can be stored in a dried form.

Freeze-drying of vesicular compositions is possible and, for this, formulation excipients are generally included in the composition to aid the drying technique. Such excipients generally serve one of two functions. Bulking agents are added to increase the total solids content in order to achieve a mechanically more robust product. Stabilizers, otherwise referred to as cryoprotectants or lyoprotectants, are added to aid the formation of the glassy state produced during dehydration and to provide physical strength in the dried product. Examples of stabilizers used in this way include mannitol and glucose.

Freeze-dried vesicular ultrasound contrast agents while providing advantages for transport and storage due to the reduction in bulk relative to the aqueous ready-to-use dispersions, also provide problems since the freeze-dried product is not thermally stable in the range of ambient temperatures normally encountered during transportation and storage and as a result must be maintained, prior to secondary production, in an environment in which the temperature is maintained below ambient (eg. at 5 to 10° C.).

It has now surprisingly been found that by appropriate choice of the stabilizer used for freeze-drying it is possible to produce freeze-dried vesicular ultrasound contrast agents which are thermally stable at ambient temperatures and above, and indeed at all temperatures normally encountered during transportation and storage.

The thermally stable freeze-dried product may then be stored and transported without need of temperature control of its environment and in particular may be supplied to hospitals and physicians for on site formulation into an administrable dispersion without requiring such users to have special storage facilities.

Thus viewed from one aspect the invention provides a freeze-dried vesicle containing ultrasound contrast agent containing a freeze-drying stabilizer and thermally stable at temperatures in excess of 20° C., preferably at least 22° C., especially 22° C., at least 25° C., more preferably at least 30° C. and especially preferably at least 40° C., eg. up to 65° C. or higher. Alternatively viewed the invention provides a freeze-dried vesicle containing ultrasound contrast agent containing a freeze-drying stabilizer and having a glass transition temperature (Tg) above 20° C., preferably 22° C., especially preferably at least 25° C., more preferably at least 30° C. and especially preferably at least 40° C., eg. up to 65° C. or higher.

Viewed from a further aspect the invention provides a process for the preparation of a thermally stable freeze-dried vesicle containing ultrasound contrast agent, which process comprises freeze-drying an aqueous dispersion comprising a vesicular ultrasound contrast agent and a freeze-drying stabilizer or mixture of stabilizers, characterised in that said stabilizer or mixture of stabilizers has a Tg value of at least 20° C. (preferably at least 22° C., especially at least 25° C., more preferably at least 30° C. and especially preferably at least 40° C., eg. up to 65° C. or higher) and a Tg' value of −37° C. or above (preferably above −36° C., especially preferably above −35° C., eg. −10 to −37° C.).

Viewed from a still further aspect the invention provides an ultrasound contrast medium comprising an aqueous carrier medium, a freeze-drying stabilizer or mixture of stabilizers and an echogenic vesicular ultrasound contrast agent, characterised in that said stabilizer or mixture of stabilizers has a Tg value of at least 20° C., (preferably at least 22° C., especially at least 25° C., more preferably at least 30° C. and especially preferably at least 40° C., eg. up to 65° C. or higher) and a Tg' value of −37° C. or above (preferably above −36° C., especially preferably above −35° C., eg. −10 to −37° C.).

Viewed from a yet still further aspect the invention provides the use of a freeze-drying stabilizer or mixture of stabilizers having a Tg value of at least 20° C., (preferably at least 22° C., especially at least 25° C., more preferably at least 30° C. and especially preferably at least 40° C., eg. up to 65° C. or higher) and a Tg' value of −370° C. or above (preferably above −36° C., especially preferably above −35° C., eg. −10 to −37° C.) for the manufacture of a vesicle containing ultrasound contrast medium for use in diagnosis involving diagnostic ultrasound imaging.

Viewed from a further aspect the invention provides a process for the storage or transportation of a vesicular ultrasound contrast agent, characterized in that said agent is in freeze-dried form, contains a freeze-drying stabilizer and has a glass transition temperature (Tg) of at least 20° C. (preferably at leat 22° C., etc.), and in that storage and transportation takes place without cooling.

Viewed from a still further aspect the invention provides a process for the preparation of a vesicle containing ultrasound contrast medium, said process comprising dispersing a freeze-dried contrast agent according to the invention in physiologically tolerable aqueous dispersion medium.

For any material, Tg is the glass transition temperature of the dried material while Tg' is the glass transition temperature of the maximally freeze-concentrated pure aqueous solution of the material.

Besides the improved thermal stability, the freeze-dried vesicular contrast agents according to the invention also surprisingly enhance the ability of the vesicles to retain the halocarbon gases and gas precursors commonly used in ultrasound contrast agents.

In the invention, the ultrasound contrast agent may be any physiologically tolerable echogenic vesicular agent, preferably however the vesicles will contain a gas or gas precursor (eg. a compound or compound mixture which is substantially in gaseous (including vapour) form at normal human body temperatures (37° C.)). Any biocompatible gas, gas precursor or mixture may be employed. The gas may thus, for example, comprise air; nitrogen; oxygen; carbon dioxide; hydrogen; nitrous oxide; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. At least some of the halogen atoms in halogenated gases advantageously are fluorine atoms. Thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include fluorinated, e.g. perfluorinated, ketones such as perfluoroacetone and fluorinated, e.g. perfluorinated, ethers such as perfluorodiethyl ether.

Particularly preferably, the vesicles will contain a perfluoroalkane, especially a perfluorobutane, perfluoropentane or perfluorohexane, in particular n-perfluorobutane.

In the vesicles, the membrane may be formed of any physiologically tolerable membrane forming material, in particular phospholipids, and may be cross-linked or non-cross-linked. Membranes formed of mixtures of charged and non-charged phospholipids are especially preferred and it is particularly preferred that the vesicles should carry a net surface charge, preferably a negative charge. Such phospholipid vesicles have particularly favourable blood residence times.

The vesicles may further be provided with a blood residence prolonging agent, eg. by conjugating such an agent to the membrane or to a lipophilic group which will anchor within the membrane. Such blood residence prolonging agents, eg. polyalkylene oxides such as polyethylene glycol, can act as opsonisation inhibitors delaying the uptake of the vesicles from the vasculature by the reticuloendothelial system.

Desirably at least 75%, preferably substantially all of the phospholipid material in the contrast agents of the invention consists of molecules which individually bear a net overall charge under conditions of preparation and/or use, which charge may be positive or, more preferably, negative. Representative positively charged phospholipids include esters of phosphatidic acids such as dipalmitoylphosphatidic acid or distearoylphosphatidic acid with aminoalcohols such as hydroxyethylenediamine. Examples of negatively charged phospholipids include naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins. The fatty acyl groups of such phospholipids will typically each contain about 14–22 carbon atoms, for example as in palmitoyl and stearoyl groups. Lyso forms of such charged phospholipids are also useful in accordance with the invention, the term "lyso" denoting phospholipids containing only one fatty acyl group, this preferably being ester-linked to the 1-position carbon atom of the glyceryl moiety. Such lyso forms of charged phospholipids may advantageously be used in admixture with charged phospholipids containing two fatty acyl groups.

Phosphatidylserines represent particularly preferred phospholipids for use in contrast agents according to the invention and preferably constitute a substantial part, e.g. at least 80% of the initial phospholipid content thereof, for example 85–92%, although this may subsequently be reduced somewhat, e.g. to ca. 70%, in subsequent processing such as heat sterilisation. While we do not wish to be bound by theoretical considerations, it may be that ionic bridging between the carboxyl and amino groups of adjacent serine moieties contributes to the stability of such systems. Preferred phosphatidylserines include saturated (e.g. hydrogenated or synthetic) natural phosphatidylserine and synthetic or semisynthetic dialkanoylphosphatidylserines such as distearoyl-phosphatidylserine, dipalmitoylphosphatidylserine and diarachidoylphosphatidylserine.

An important advantage of the use of such phosphatidylserine-based contrast agents is that the body recognises aged red blood cells and platelets by high concentrations of phosphatidylserine on their surface and so may eliminate such contrast agents from the blood stream in a manner similar to the elimination of aged red blood cells. Furthermore, since the surface of such contrast agents may be registered as endogenous by the body, they may avoid induction of adverse systemic side effects such as haemodynamic effects and other anaphylactic reactions which may accompany administration of some liposome preparations (see e.g. WO-A-95/12386).

Liposomal ultrasound contrast agents suitable for use according to the invention may be prepared as described in the literature, see for example WO-A-92/22247, WO-A-94/28780, WO-A-93/05819, WO-A-95/16467, PCT/GB96/01361 and Unger et al. Invest. Radiol. 29 (Suppl. 2): S134–S136 (1994).

The stabilizer used according to the invention may be a physiologically tolerable freeze-drying stabilizer (or mixture) having a glass transition temperature (Tg) above 20° C., eg. in the range 25 to 70° C., and having a Tg' value of −37° C. or above. Examples of suitable stabilizers include sucrose, maltose $H_2O$, trehalose, raffinose and stachyose. One particularly suitable example is sucrose, optionally in admixture with minor quantities (eg. up to 20% by weight, preferably up to 10% by weight) of other stabilizers.

In general the stabilizer will be present in the composition being freeze-dried at a concentration significantly in excess of that of the vesicular contrast agent, eg. at a weight ratio of at least 10:1, more normally at least 20:1, optimally as high as 200:1, eg. up to 5000:1 or even higher. Accordingly, the contribution to the glass transition temperature (Tg) of the dried product is relatively independent of the vesicular component and candidate stabilizers can be screened easily by routine techniques to determine whether they, in combination with the other excipients present in the aqueous carrier medium, dry to form a product having a glass transition temperature (Tg) above 20° C.

Conveniently the stabilizer will be present at 1 to 50% by weight, preferably 5 to 30%, more especially about 10 to 20% by weight, in the composition undergoing freeze-drying. The concentration of stabilizer may if desired be well in excess of isotonic concentrations since, on reconstitution after freeze-drying, the product can be diluted. The vesicle component will preferably be present at 0.01 to 5% by weight, preferably 0.1 to 3%, especially preferably about 0.5 to 1.5% by weight (considering its weight to be only the weight of the membrane forming material). The quantity of stabilizer relative to the reconstitution fluid used to transform the freeze-dried product into an administrable dispersion will be selected dependent on the body region or organ to be imaged and on the administration mode chosen. By way of example it may be at least twice that in the composition which underwent freeze-drying.

For ultrasound applications such as echocardiography, in order to permit free passage through the pulmonary system and to achieve resonance with the preferred imaging frequencies of about 0.1–15 MHz, it may be convenient to employ vesicles having an average size of 0.1–10 μm, e.g. 1–7 μm. The vesicles may be produced with a very narrow size distribution within the range preferred for echocardiography, thereby greatly enhancing their echogenicity as well as their safety in vivo, and rendering the contrast agents of particular advantage in applications such as blood pressure measurements, blood flow tracing and ultrasound tomography. Thus, for example, products in which over 90% (e.g. at least 95%, preferably at least 98%) of the vesicles have diameters in the range 1–7 μm and less than 5% (e.g. not more than 3%, preferably not more than 2%) of the vesicles have diameters above 7 μm may readily be prepared.

In ultrasound applications the contrast media may, for example, be administered in doses such that the amount of membrane forming material (eg. phospholipid) injected is in the range 0.1–10 μg/kg body weight, more preferably 1–5 μg/kg. It will be appreciated that the use of such low levels of membrane forming material is of substantial advantage in minimising possible toxic side effects.

The overall membrane forming material concentration in ready-to-use compositions made using the dried product of the invention will desirably be in the range 0.01 to 5% by weight, preferably 0.05 to 2.0% and particularly about 0.5% by weight.

The composition subjected to freeze-drying will advantageously contain at least one bulking agent, eg. a polyol (eg. a $C_3$ polyol such as glycerol or propylene glycol) or a polysaccharide such as dextran, or a polyglycol such as polyethylene glycol or mixtures thereof. Typically the bulking agent may be used in concentrations similar to or slightly less than that of the stabilizer, eg. 3 to 10% by weight, preferably about 5% by weight. The bulking agents should be able to crystallize during the freeze-drying process as only in this state do they have a neutral effect on product stability. They are thus distinguished from the stabilizers which should be present in the amorphous state during freeze-drying.

Other excipients may if desired by present in the composition being dried or may be added on formulation for administration. Such excipients may for example include pH regulators, osmolality adjusters, viscosity enhancers, emulsifiers, etc. and may be used in conventional amounts.

The dried product will generally be in powder form and is readily reconstitutable in water, an aqueous solution such as saline (which may advantageously be balanced so that the final product for injection is not hypotonic), or a solution of one or more tonicity adjusting substances such as salts (eg. of plasma cations with physiologically tolerable counterions), or sugars, sugar alcohols, glycols and other non-ionic polyol materials (eg. glucose, sucrose, sorbitol, mannitol, glycerol, polyethylene glycols, propylene glycols and the like). Reconstitution will generally require only minimal agitation such as may, for example, be provided by gentle hand-shaking. The size of the vesicles so generated is consistently reproducible and in practice is independent of the amount of agitational energy applied, being determined by the size of the vesicles formed in the initial vesicle dispersion, this size parameter surprisingly being substantially maintained in the lyophilised and reconstituted product. Thus, since the size of the vesicles in the initial dispersion may readily be controlled by process parameters such as the method, speed and duration of agitation, the final vesicle size may readily be controlled.

The volume and concentrations of the reconstitution liquid may desirably be balanced to make the resulting ready-to-use formulations substantially isotonic. Hence the volume and concentration of reconstitution fluid chosen will be dependent on the type and amount of stabilizer (and other bulking agents) present in the freeze-dried product.

Lyophilised products according to the invention have proved to be storage stable for several months under ambient conditions. The vesicle dispersions generated upon reconstitution in water (or other reconstitution liquids as discussed above) may be stable for considerable lengths of time, eg. up to at least 12 hours, permitting considerable flexibility as to when the dried product is reconstituted prior to injection.

If the reconstitution liquid contains as a tonicity adjuster the same compound as is used as a stabilizer in the lyophilization, the amount of stabilizer present in the composition for freeze-drying need only be sufficient to give the optimal stabilization during freeze-drying. Isotonicity of the final product may thus be obtained by selecting an adequate amount and concentration of the reconstitution liquid. Hence a considerable flexibility is permitted as to the concentration and type of compound(s) to be used as stabilizer(s) during the freeze-drying step, and concentration and type of compound(s) in the reconstitution liquid, while still achieving a stable reconstituted product.

Freeze-drying according to the invention may be effected in a conventional manner although using stabilizers according to the invention may have the added advantage that, since the compositions before drying generally have higher glass temperatures (Tg') than equivalent compositions containing cryoprotectants such as glucose or mannitol, shorter freeze-drying cycles may be used.

The invention has been described above with reference to vesicular ultrasound contrast agents. However it is also applicable to vesicular contrast agents for other diagnostic imaging modalities (eg. MRI, X-ray, SPECT, PET, magnetographic imaging etc.).

The invention will now be described further with reference to the following non-limiting Examples:

EXAMPLE 1

Preparation of Lyophilized Product 500.4 mg hydrogenated egg phosphatidylserine was added to 100 ml water containing 5.4% (w/w) of a mixture of propylene glycol and glycerol (3:10 w/w). The mixture was shaken and heated to 80° C. for five minutes, allowed to cool to room temperature, shaken again and left standing overnight prior to use. 50 ml of the resulting solution was transferred to a round-bottomed flask with a conical neck.

The flask was fitted with a glass jacket having a temperature control inlet and outlet connected to a water bath maintained at 25° C. A rotor stator mixing shaft was introduced into the solution and to avoid gas leakage the space between the neck wall and the mixing shaft was sealed with a specially designed metal plug fitted with a gas inlet/outlet connection for adjustment of gas content and pressure control. The gas outlet was connected to a vacuum pump and the solution was degassed for one minute. An atmosphere of perfluoro-n-butane gas was then applied through the gas inlet.

The solution was homogenised at 23000 rpm for 10 minutes, keeping the rotor stator mixing shaft such that the openings were slightly above the surface of the liquid. A white coloured creamy dispersion was obtained, which was transferred to a sealable container and flushed with perfluoro-n-butane. The dispersion was then transferred to a separating funnel and centrifuged at 12000 rpm for 30 minutes, yielding a creamy layer of bubbles at the top and a turbid infranatant. The infranatant was removed and replaced with water. The centrifugation was then repeated twice, but now at 12000 rpm for 15 minutes. After the last centrifugation, the supernatant was replaced by 10% (w/w) sucrose. 2 ml portions of the resulting dispersion were divided between 10 ml flat-bottomed vials specially designed for lyophilisation, and the vials were cooled to −47° C. and lyophilised for approximately 48 hours, giving a white fluffy solid substance. The vials were transferred to a vacuum chamber, and air was removed by a vacuum pump and replaced by perfluoro-n-butane gas. Prior to use, water was added and the vials were gently hand-shaken for several seconds, giving microbubble dispersions suitable as ultrasound contrast agents.

Characterisation

The size distribution and volume concentration of the microbubbles were measured using a Coulter Counter Mark II apparatus fitted with a 50 μm aperture with a measuring range of 1–30 μm. 20 μl samples were diluted in 200 ml saline saturated with air at room temperature, and allowed to equilibrate for 3 minutes prior to measurement.

Ultrasound characterisation was performed on a experimental set up slightly modified from de Jong, N. and Hoff, Ultrasonics, 31: 175–181 (1993). This instrumentation measures the ultrasound attenuation efficacy in the frequency range 2–8 MHz of a dilute suspension of contrast agent. During the attenuation measurement a pressure stability test was performed by exposing the sample to an overpressure of 120 mmHg for 90 seconds. Typically 2–3 μl of sample was diluted in 55 ml Isoton II and the diluted sample suspension was stirred for 3 minutes prior to analysis. As primary response parameter the attenuation at 3.5 MHz was used, together with the recovery attenuation value at 3.5 MHz after release of the overpressure.

TABLE 1

In vitro characteristics of bubble dispersions produced according to Example 1. Number and volume weighted concentrations and volume mean diameters. Acoustic properties measured according to description above.

| Number conc. [10⁶/ml] | Vol. conc. [%] | Vol. mean diam. [μm] | Atten. at 3.5 Mhz [db/cm] | Survival after over-pressure [%] | Freq. at max. atten. [MHz] |
|---|---|---|---|---|---|
| 10518 | 6.51 | 3.16 | 150.4 | 96 | 4.3 |

EXAMPLE 2

The gas contents of five samples prepared according to Example 1 above were replaced with air, perfluorobutane, sulphur hexafluoride, trifluoromethylsulphur pentafluoride and tetramethylsilane respectively, according to the following procedure:

Two samples containing lyophilised product from Example 1 were placed in a desiccator having a gas inlet and a gas outlet. The desiccator was connected to a Büchi 168 vacuum/distiller controller which permitted controlled evacuation of the samples and inlet of a selected gas. The samples were evacuated at approximately 10 mbar for 5 minutes, whereafter the pressure was increased to atmospheric by inlet of the selected gas, followed by careful capping of the vials. The procedure was repeated using further pairs of samples for each of the selected gases.

2 ml distilled water was added to each vial and the vials were gently hand-shaken prior to use. The resulting microbubble dispersions were characterised with respect to size distribution measurements as described in Example 1. The results are summarised in Table 2.

TABLE 2

In vitro characteristics of phosphatidylserine-stabilised microbubble dispersions produced according to Example 2 - number and volume weighted concentrations and volume mean diameters.

| Gas | Number conc. [10⁶/ml] | Number mean diam. [μm] | Vol. conc. [%] | Vol. mean diam. [μm] |
|---|---|---|---|---|
| Perfluorobutane | 9756 | 1.8 | 4.9 | 5.8 |
| Trifluoromethyl-sulphur pentafluoride | 10243 | 1.9 | 5.9 | 3.5 |
| Sulphur hexafluoride | 9927 | 1.9 | 5.7 | 3.2 |
| Tetramethylsilane | 9947 | 1.9 | 6.1 | 3.7 |
| Air | 9909 | 1.9 | 6.4 | 4.0 |

As will be seem from the above results there is no significant change in size distribution upon gas exchange, demonstrating that the preformed microbubble size is substantially preserved during both lyophilisation and reconstitution.

In Vivo Results

One batch prepared with each of the five gases was evaluated in vivo for Doppler enhancement properties at 10 MHz. The dispersions were injected into chinchilla rabbits via an ear vein and measured using a Doppler technique where an ultrasound probe is placed directly on a carotid artery. Signal intensities and duration were recorded and the integral of the Doppler curve is calculated. The results obtained (see Table 3 below) show that microbubbles containing perfluorobutane give the strongest Doppler intensity enhancement. Microbubbles containing sulphur hexafluoride, trifluoromethylsulphur pentafluoride or tetramethylsilane are only slightly less efficacious as Doppler enhancers than those containing perfluorobutane, giving integrals in the range 60–80% of the figure for perfluorobutane.

TABLE 3

Results for i.v. injections of Example 2 products into rabbits. The values are adjusted for drift in baseline. The Doppler unit is defined as the increase in Doppler signal relative to that of blood.

| Gas | Integrated Arterial Doppler Enhancement (NDU.s) |
| --- | --- |
| Perfluorobutane* | 10361 |
| Trifluoromethylsulphur pentafluoride | 8006 |
| Tetramethylsilane | 6370 |
| Sulphur hexafluoride | 6297 |
| Air | 1024 |

*Average of two injections

EXAMPLE 3

A vial containing lyophilised material under an atmosphere of perfluorobutane was prepared as described in Example 1. Water was added to the vial just before use to give a microbubble suspension.

200 ml Isoton II fluid was exposed to air for several days at room temperature to give a fully air-saturated solution. Another 200 ml of the fluid was degassed in a vacuum flask at 60° C. for one hour and cooled to room temperature while maintaining the vacuum. Air was admitted to the flask immediately prior to use.

10 μl portions of the microbubble suspension were added to each of the fluids and the resulting mixtures was incubated for 5 minutes prior to size characterisation (Coulter Multisizer Mark II).

In the degassed environment, where no diffusion of gases from the fluid into the microbubbles was expected, the mean microbubble diameter was 1.77 μm and 0.25% of the microbubbles are larger than 5 μm. In the air-saturated fluid the corresponding values were 2.43 μm and 0.67%; repeated measurements made after a further 5 minutes indicate that the microbubble sizes had reached a stable value.

These findings show that the average diameter of the microbubbles increases by only 37% when they are exposed to an air-saturated fluid analogous to arterial blood, with very few microbubbles reaching a size which might cause blockage of capillary blood vessels. This may be contrasted with the doubling in size of air/perfluorohexane-containing microbubbles in a similar environment (i.e. a highly diluted dispersion of microbubbles in water containing dissolved air) reported in Example II of WO-A-95/03835.

EXAMPLE 4

Comparison

Example 1 was repeated replacing the supernatant before lyophilization instead with (a) 65 mg/mL sucrose plus 65 mg/mL mannitol, (b) 100 mg/mL mannitol plus 50 mg/mL glucose, (c) 20 mg/mL sucrose, 76 mg/mL mannitol and 38 mg/mL glucose, and (d) 90 mg/mL sucrose.

The Tg' and Tg values of the wet and dried compositions were determined and are set out in Table 4 below.

TABLE 4

| Formulation | Tg' | Tg |
| --- | --- | --- |
| (a) | −38° C. | 19° C. |
| (b) | −43° C. | 14° C. |
| (c) | −42° C. | 12° C. |
| (d) | −32° C. | 66° C. |

Formulations (a) to (c) need longer freeze-drying cycles than formulation (d) and unlike formulation (d) must be stored below ambient temperature to maintain their integrity.

EXAMPLES 5

Gas Retention

Material produced analogously to Example 1 but using (a) 10% (w/w) sucrose, (b) 5% (w/w) PEG 3000, (c) 2% (w/w) mannitol and 1% (w/w) glucose, and (d) 5% (w/w) trehalose to replace the supernatant prior to lyophilization was exposed to extensive flushing with $N_2$, exposure to repeated vacuum cycles, and crushing to test the ability of the product to retain perfluorobutane.

After stress treatment the remaining perfluorobutane content was determined. The results are set out in Table 5 below.

TABLE 5

| Cryoprotectant | mg PFB/g product |
| --- | --- |
| Sucrose | 0.69 ± 0.10 |
| PEG 3000 | ≦0.05 |
| Mannitol + glucose | 0.29 ± 0.10 |
| Trehalose | 1.24 ± 0.38 |

In the foregoing examples, higher percentages of stabilizer (eg. 20% rather than 10%) may be used and other reconstitution fluids than water, eg. the saline or polyol solutions referred to above may be used. Similarly, the portions that are lyophilized may be larger (eg. 4 mL rather than 2 mL), lyophilization vials may be larger (eg. 20 mL) and lyophilization may be longer (eg. 60 hours).

What is claimed is:

1. A freeze-dried vesicle-containing ultrasound contrast agent containing at least one bulking agent selected from the group consisting of glycerol, propylene glycol, dextran and polyethylene glycol and at least one freeze-drying stabilizer selected from the group consisting of sucrose, maltose.$H_2O$, trehalose, raffinose and stachyose, wherein the weight ratio of said stabilizer to the vesicles in said agent is at least 10:1, and said agent has a Tg value in excess of 20° C, a Tg' value of −37° C or above, and is thermally stable at temperatures in excess of 20° C.

2. A contrast agent as claimed in claim 1 wherein said stabilizer comprises sucrose.

3. A contrast agent as claimed in claim 1 wherein the weight ratio of said stabilizer to the vesicles in said agent is at least 20:1.

4. A contrast agent as claimed in claim 1 wherein the vesicles contain a halocarbon gas or gas precursor or a sulphur fluoride gas.

5. A contrast agent as claimed in claim 4 wherein said halocarbon gas or gas precursor is a perfluoroalkane.

6. A contrast agent as claimed in claim 5 wherein said perfluoroalkane is selected from the group consisting of perfluorobutane and perfluoropentane.

7. A contrast agent as claimed in claim 4 wherein said sulphur fluoride gas is selected from the group consisting of sulphur hexafluoride, disulphur decafluoride and trifluoromethylsulphur pentafluoride.

8. A contrast agent as claimed in claim 1 wherein the vesicles have membranes which comprise a phospholipid.

9. A process for the preparation of a freeze-dried vesicle-containing ultrasound contrast agent as claimed in claim 1, said process comprising freeze-drying an aqueous dispersion comprising a vesicular ultrasound contrast agent, at least one bulking agent selected from the group consisting of glycerol, propylene glycol, dextran and polyethylene glycol and at least one freeze-drying stabilizer selected from the group consisting of sucrose, maltose.$H_2O$, trehalose, raffinose and stachyose, wherein said stabilizer is present in said dispersion in a weight ratio relative to the vesicles therein of at least 10:1.

10. A process as claimed in claim 9 wherein said aqueous dispersion contains from 1 to 50% by weight of said stabilizer.

11. A process as claimed in claim 9 wherein said vesicular contrast agent contains a halocarbon gas or gas precursor or a sulphur fluoride gas.

12. A process as claimed in claim 11 wherein said halocarbon gas or gas precursor is selected from the group consisting of perfluorobutane and perfluoropentane.

13. A process as claimed in claim 11 wherein said sulphur fluoride gas is selected from the group consisting of sulphur hexafluoride, disulphur decafluoride and trifluoromethylsulphur pentafluoride.

14. A process as claimed in claim 9 wherein said aqueous dispersion contains 3 to 10% by weight of said bulking agent.

15. A process for the storage or transportation of a freeze-dried vesicle-containing ultrasound contrast agent as defined in claim 1 wherein said storage or transport takes place without use of cooling.

16. A process for the preparation of an injectable vesicle-containing ultrasound contrast agent which comprises dispersing a freeze-dried vesicle-containing ultrasound contrast agent as defined in claim 1 in a physiologically tolerable injectable aqueous carrier medium.

17. A method of diagnosis of a mammal involving diagnostic ultrasound imaging, which method comprises administering a vesicle-containing ultrasound contrast agent containing at least one bulking agent selected from the group consisting of glycerol, propylene glycol, dextran and polyethylene glycol and at least one freeze-drying stabilizer selected from the group consisting-of sucrose, maltose.$H_2O$, trehalose, raffinose and stachyose, wherein the weight ratio of said stabilizer to the vesicles in said agent is at least 10:1, and said agent has a Tg value in excess of 20° C, a Tg' value of −37° C or above, and is thermally stable at temperatures in excess of 20° C., and performing ultrasound imaging.

\* \* \* \* \*